(12) United States Patent
Penna et al.

(10) Patent No.: US 10,881,408 B2
(45) Date of Patent: Jan. 5, 2021

(54) INTERLOCK ASSEMBLY FOR REPLACEABLE LOADING UNITS

(71) Applicant: Covidien LP, Mansfield, MA (US)

(72) Inventors: Christopher Penna, Guilford, CT (US); Michael Bettuchi, Madison, CT (US)

(73) Assignee: Covidien LP, Mansfield, MA (US)

( * ) Notice: Subject to any disclaimer, the term of this patent is extended or adjusted under 35 U.S.C. 154(b) by 1075 days.

(21) Appl. No.: 15/074,045

(22) Filed: Mar. 18, 2016

(65) Prior Publication Data

US 2016/0310141 A1 Oct. 27, 2016

Related U.S. Application Data

(60) Provisional application No. 62/150,913, filed on Apr. 22, 2015.

(51) Int. Cl.
| | |
|---|---|
| *A61B 17/10* | (2006.01) |
| *A61B 17/068* | (2006.01) |
| *A61B 17/115* | (2006.01) |
| *A61B 17/00* | (2006.01) |

(52) U.S. Cl.
CPC ... *A61B 17/1155* (2013.01); *A61B 2017/0046* (2013.01); *A61B 2017/00473* (2013.01); *A61B 2017/00477* (2013.01)

(58) Field of Classification Search
CPC . A61B 17/1155; A61B 17/105; A61B 17/068; A61B 2017/00473; A61B 2017/0046; A61B 2017/00477; F16B 7/042; F16B 7/1454
USPC .............................. 403/109.2, 321, 330, 377
See application file for complete search history.

(56) References Cited

U.S. PATENT DOCUMENTS

| | | | |
|---|---|---|---|
| 3,193,165 A | 7/1965 | Akhalaya et al. | |
| 3,388,847 A | 6/1968 | Kasulin et al. | |
| 3,552,626 A | 1/1971 | Astafiev et al. | |
| 3,638,652 A | 2/1972 | Kelley | |
| 3,771,526 A | 11/1973 | Rudie | |
| 3,867,055 A * | 2/1975 | Wooden | F16B 2/08 24/20 S |
| 4,198,982 A | 4/1980 | Fortner et al. | |
| 4,207,898 A | 6/1980 | Becht | |
| 4,289,133 A | 9/1981 | Rothfuss | |

(Continued)

FOREIGN PATENT DOCUMENTS

| | | |
|---|---|---|
| AU | 2014101295 A4 | 11/2014 |
| AU | 2015252008 A1 | 6/2016 |

(Continued)

OTHER PUBLICATIONS

European Search Report dated Jun. 24, 2016, issued in EP Application No. 16150288.5.

(Continued)

*Primary Examiner* — Thomas M Wittenschlaeger
(74) *Attorney, Agent, or Firm* — Carter, DeLuca & Farrell LLP (57) ABSTRACT

A loading unit including interlock assembly for attaching the loading unit to a surgical stapling instrument is provided. The interlock assembly is formed on a proximal end of a shell member and includes a collar member pivotally secured to the shell member. The collar member selectively secures the shell member to the adapter assembly.

20 Claims, 8 Drawing Sheets

(56) References Cited

U.S. PATENT DOCUMENTS

| | | |
|---|---|---|
| 4,304,236 A | 12/1981 | Conta et al. |
| 4,319,576 A | 3/1982 | Rothfuss |
| 4,350,160 A | 9/1982 | Kolesov et al. |
| 4,351,466 A | 9/1982 | Noiles |
| 4,361,314 A * | 11/1982 | Ohlson .................. E01F 8/007 256/65.02 |
| 4,379,457 A | 4/1983 | Gravener et al. |
| 4,473,077 A | 9/1984 | Noiles et al. |
| 4,476,863 A | 10/1984 | Kanshin et al. |
| 4,485,817 A | 12/1984 | Swiggett |
| 4,488,523 A | 12/1984 | Shichman |
| 4,505,272 A | 3/1985 | Utyamyshev et al. |
| 4,505,414 A | 3/1985 | Filipi |
| 4,520,817 A | 6/1985 | Green |
| 4,550,870 A | 11/1985 | Krumme et al. |
| 4,573,468 A | 3/1986 | Conta et al. |
| 4,576,167 A | 3/1986 | Noiles |
| 4,592,354 A | 6/1986 | Rothfuss |
| 4,603,693 A | 8/1986 | Conta et al. |
| 4,606,343 A | 8/1986 | Conta et al. |
| 4,632,290 A | 12/1986 | Green et al. |
| 4,646,745 A | 3/1987 | Noiles |
| 4,665,917 A | 5/1987 | Clanton et al. |
| 4,667,673 A | 5/1987 | Li |
| 4,671,445 A | 6/1987 | Barker et al. |
| 4,700,703 A | 10/1987 | Resnick et al. |
| 4,703,887 A | 11/1987 | Clanton et al. |
| 4,708,141 A | 11/1987 | Inoue et al. |
| 4,717,063 A | 1/1988 | Ebihara |
| 4,752,024 A | 6/1988 | Green et al. |
| 4,754,909 A | 7/1988 | Barker et al. |
| 4,776,506 A | 10/1988 | Green |
| 4,817,847 A | 4/1989 | Redtenbacher et al. |
| 4,873,977 A | 10/1989 | Avant et al. |
| 4,893,662 A | 1/1990 | Gervasi |
| 4,903,697 A | 2/1990 | Resnick et al. |
| 4,907,591 A | 3/1990 | Vasconcellos et al. |
| 4,917,114 A | 4/1990 | Green et al. |
| 4,957,499 A | 9/1990 | Lipatov et al. |
| 4,962,877 A | 10/1990 | Hervas |
| 5,005,749 A | 4/1991 | Aranyi |
| 5,042,707 A | 8/1991 | Taheri |
| 5,047,039 A | 9/1991 | Avant et al. |
| 5,104,025 A | 4/1992 | Main et al. |
| 5,119,983 A | 6/1992 | Green et al. |
| 5,122,156 A | 6/1992 | Granger et al. |
| 5,139,513 A | 8/1992 | Segato |
| 5,158,222 A | 10/1992 | Green et al. |
| 5,188,638 A | 2/1993 | Tzakis |
| 5,193,731 A | 3/1993 | Aranyi |
| 5,197,648 A | 3/1993 | Gingold |
| 5,197,649 A | 3/1993 | Bessler et al. |
| 5,205,459 A | 4/1993 | Brinkerhoff et al. |
| 5,221,036 A | 6/1993 | Takase |
| 5,222,963 A | 6/1993 | Brinkerhoff et al. |
| 5,253,793 A | 10/1993 | Green et al. |
| 5,261,920 A | 11/1993 | Main et al. |
| 5,271,543 A | 12/1993 | Grant et al. |
| 5,271,544 A | 12/1993 | Fox et al. |
| 5,275,322 A | 1/1994 | Brinkerhoff et al. |
| 5,282,810 A | 2/1994 | Allen et al. |
| 5,285,944 A | 2/1994 | Green et al. |
| 5,285,945 A | 2/1994 | Brinkerhoff et al. |
| 5,292,053 A | 3/1994 | Bilotti et al. |
| 5,309,927 A | 5/1994 | Welch |
| 5,312,024 A | 5/1994 | Grant et al. |
| 5,314,435 A | 5/1994 | Green et al. |
| 5,314,436 A | 5/1994 | Wilk |
| 5,330,486 A | 7/1994 | Wilk |
| 5,333,773 A | 8/1994 | Main et al. |
| 5,344,059 A | 9/1994 | Green et al. |
| 5,346,115 A | 9/1994 | Perouse et al. |
| 5,348,259 A | 9/1994 | Blanco et al. |
| 5,350,104 A | 9/1994 | Main et al. |
| 5,355,897 A | 10/1994 | Pietrafitta et al. |
| 5,360,154 A | 11/1994 | Green |
| 5,368,215 A | 11/1994 | Green et al. |
| 5,392,979 A | 2/1995 | Green et al. |
| 5,395,030 A | 3/1995 | Kuramoto et al. |
| 5,403,333 A | 4/1995 | Kaster et al. |
| 5,404,870 A | 4/1995 | Brinkerhoff et al. |
| 5,411,508 A | 5/1995 | Bessler et al. |
| 5,425,738 A | 6/1995 | Gustafson et al. |
| 5,433,721 A | 7/1995 | Hooven et al. |
| 5,437,684 A | 8/1995 | Calabrese et al. |
| 5,439,156 A | 8/1995 | Grant et al. |
| 5,443,198 A | 8/1995 | Viola et al. |
| 5,447,514 A | 9/1995 | Gerry et al. |
| 5,454,825 A | 10/1995 | Van Leeuwen et al. |
| 5,464,415 A | 11/1995 | Chen |
| 5,470,006 A | 11/1995 | Rodak |
| 5,474,223 A | 12/1995 | Viola et al. |
| 5,497,934 A | 3/1996 | Brady et al. |
| 5,503,635 A | 4/1996 | Sauer et al. |
| 5,522,534 A | 6/1996 | Viola et al. |
| 5,533,661 A | 7/1996 | Main et al. |
| 5,588,579 A | 12/1996 | Schnut et al. |
| 5,609,285 A | 3/1997 | Grant et al. |
| 5,626,591 A | 5/1997 | Kockerling et al. |
| 5,632,433 A | 5/1997 | Grant et al. |
| 5,639,008 A | 6/1997 | Gallagher et al. |
| 5,641,111 A | 6/1997 | Ahrens et al. |
| 5,658,300 A | 8/1997 | Bito et al. |
| 5,669,918 A | 9/1997 | Balazs et al. |
| 5,685,474 A | 11/1997 | Seeber |
| 5,709,335 A | 1/1998 | Heck |
| 5,715,987 A | 2/1998 | Kelley et al. |
| 5,718,360 A | 2/1998 | Green et al. |
| 5,720,755 A | 2/1998 | Dakov |
| 5,732,872 A | 3/1998 | Bolduc et al. |
| 5,749,896 A | 5/1998 | Cook |
| 5,758,814 A | 6/1998 | Gallagher et al. |
| 5,772,355 A * | 6/1998 | Ross ..................... G02B 23/24 359/818 |
| 5,799,857 A | 9/1998 | Robertson et al. |
| 5,814,055 A | 9/1998 | Knodel et al. |
| 5,833,698 A | 11/1998 | Hinchliffe et al. |
| 5,836,503 A | 11/1998 | Ehrenfels et al. |
| 5,839,639 A | 11/1998 | Sauer et al. |
| 5,855,312 A | 1/1999 | Toledano |
| 5,860,581 A | 1/1999 | Robertson et al. |
| 5,868,760 A | 2/1999 | McGuckin, Jr. |
| 5,881,943 A | 3/1999 | Heck et al. |
| 5,915,616 A | 6/1999 | Viola et al. |
| 5,947,363 A | 9/1999 | Bolduc et al. |
| 5,951,576 A | 9/1999 | Wakabayashi |
| 5,957,363 A | 9/1999 | Heck |
| 5,993,468 A | 11/1999 | Rygaard |
| 6,024,748 A | 2/2000 | Manzo et al. |
| 6,050,472 A | 4/2000 | Shibata |
| 6,053,390 A | 4/2000 | Green et al. |
| 6,068,636 A | 5/2000 | Chen |
| 6,083,241 A | 7/2000 | Longo et al. |
| 6,102,271 A | 8/2000 | Longo et al. |
| 6,117,148 A | 9/2000 | Ravo et al. |
| 6,119,913 A | 9/2000 | Adams et al. |
| 6,126,058 A | 10/2000 | Adams et al. |
| 6,142,933 A | 11/2000 | Longo et al. |
| 6,149,667 A | 11/2000 | Hovland et al. |
| 6,176,413 B1 | 1/2001 | Heck et al. |
| 6,179,195 B1 | 1/2001 | Adams et al. |
| 6,193,129 B1 | 2/2001 | Bittner et al. |
| 6,203,553 B1 | 3/2001 | Robertson et al. |
| 6,209,773 B1 | 4/2001 | Bolduc et al. |
| 6,241,140 B1 | 6/2001 | Adams et al. |
| 6,253,984 B1 | 7/2001 | Heck et al. |
| 6,258,107 B1 | 7/2001 | Balazs et al. |
| 6,264,086 B1 | 7/2001 | McGuckin, Jr. |
| 6,269,997 B1 | 8/2001 | Balazs et al. |
| 6,273,897 B1 | 8/2001 | Dalessandro et al. |
| 6,279,809 B1 | 8/2001 | Nicolo |
| 6,302,311 B1 | 10/2001 | Adams et al. |
| 6,338,737 B1 | 1/2002 | Toledano |
| 6,343,731 B1 | 2/2002 | Adams et al. |

(56) References Cited

U.S. PATENT DOCUMENTS

| | | | |
|---|---|---|---|
| 6,387,105 B1 | 5/2002 | Gifford, III et al. |
| 6,398,795 B1 | 6/2002 | McAlister et al. |
| 6,402,008 B1 | 6/2002 | Lucas |
| 6,439,446 B1 | 8/2002 | Perry et al. |
| 6,443,973 B1 | 9/2002 | Whitman |
| 6,450,390 B2 | 9/2002 | Heck et al. |
| 6,478,210 B2 | 11/2002 | Adams et al. |
| 6,488,197 B1 | 12/2002 | Whitman |
| 6,491,201 B1 | 12/2002 | Whitman |
| 6,494,877 B2 | 12/2002 | Odell et al. |
| 6,503,259 B2 | 1/2003 | Huxel et al. |
| 6,517,566 B1 | 2/2003 | Hovland et al. |
| 6,520,398 B2 | 2/2003 | Nicolo |
| 6,533,157 B1 | 3/2003 | Whitman |
| 6,551,334 B2 | 4/2003 | Blatter et al. |
| 6,578,751 B2 | 6/2003 | Hartwick |
| 6,585,144 B2 | 7/2003 | Adams et al. |
| 6,588,643 B2 | 7/2003 | Bolduc et al. |
| 6,592,596 B1 | 7/2003 | Geitz |
| 6,601,749 B2 | 8/2003 | Sullivan et al. |
| 6,605,078 B2 | 8/2003 | Adams |
| 6,605,098 B2 | 8/2003 | Nobis et al. |
| 6,626,921 B2 | 9/2003 | Blatter et al. |
| 6,629,630 B2 | 10/2003 | Adams |
| 6,631,837 B1 | 10/2003 | Heck |
| 6,632,227 B2 | 10/2003 | Adams |
| 6,632,237 B2 | 10/2003 | Ben-David et al. |
| 6,652,542 B2 | 11/2003 | Blatter et al. |
| 6,659,327 B2 | 12/2003 | Heck et al. |
| 6,676,671 B2 | 1/2004 | Robertson et al. |
| 6,681,979 B2 | 1/2004 | Whitman |
| 6,685,079 B2 | 2/2004 | Sharma et al. |
| 6,695,198 B2 | 2/2004 | Adams et al. |
| 6,695,199 B2 | 2/2004 | Whitman |
| 6,698,643 B2 | 3/2004 | Whitman |
| 6,716,222 B2 | 4/2004 | McAlister et al. |
| 6,716,233 B1 | 4/2004 | Whitman |
| 6,726,697 B2 | 4/2004 | Nicholas et al. |
| 6,742,692 B2 | 6/2004 | Hartwick |
| 6,743,244 B2 | 6/2004 | Blatter et al. |
| 6,763,993 B2 | 7/2004 | Bolduc et al. |
| 6,769,590 B2 | 8/2004 | Vresh et al. |
| 6,769,594 B2 | 8/2004 | Orban, III |
| 6,820,791 B2 | 11/2004 | Adams |
| 6,821,282 B2 | 11/2004 | Perry et al. |
| 6,827,246 B2 | 12/2004 | Sullivan et al. |
| 6,840,423 B2 | 1/2005 | Adams et al. |
| 6,843,403 B2 | 1/2005 | Whitman |
| 6,846,308 B2 | 1/2005 | Whitman et al. |
| 6,852,122 B2 | 2/2005 | Rush |
| 6,866,178 B2 | 3/2005 | Adams et al. |
| 6,872,214 B2 | 3/2005 | Sonnenschein et al. |
| 6,874,669 B2 | 4/2005 | Adams et al. |
| 6,884,250 B2 | 4/2005 | Monassevitch et al. |
| 6,905,504 B1 | 6/2005 | Vargas |
| 6,938,814 B2 | 9/2005 | Sharma et al. |
| 6,942,675 B1 | 9/2005 | Vargas |
| 6,945,444 B2 | 9/2005 | Gresham et al. |
| 6,953,138 B1 | 10/2005 | Dworak et al. |
| 6,957,758 B2 | 10/2005 | Aranyi |
| 6,959,851 B2 | 11/2005 | Heinrich |
| 6,978,922 B2 | 12/2005 | Bilotti et al. |
| 6,981,941 B2 | 1/2006 | Whitman et al. |
| 6,981,979 B2 | 1/2006 | Nicolo |
| 7,032,798 B2 | 4/2006 | Whitman et al. |
| 7,059,331 B2 | 6/2006 | Adams et al. |
| 7,059,510 B2 | 6/2006 | Orban, III |
| 7,077,856 B2 | 7/2006 | Whitman |
| 7,080,769 B2 | 7/2006 | Vresh et al. |
| 7,086,267 B2 | 8/2006 | Dworak et al. |
| 7,114,642 B2 | 10/2006 | Whitman |
| 7,118,528 B1 | 10/2006 | Piskun |
| 7,122,044 B2 | 10/2006 | Bolduc et al. |
| 7,128,748 B2 | 10/2006 | Mooradian et al. |
| 7,141,055 B2 | 11/2006 | Abrams et al. |
| 7,168,604 B2 | 1/2007 | Milliman et al. |
| 7,179,267 B2 | 2/2007 | Nolan et al. |
| 7,182,239 B1 | 2/2007 | Myers |
| 7,195,142 B2 | 3/2007 | Orban, III |
| 7,207,168 B2 | 4/2007 | Doepker et al. |
| 7,220,237 B2 | 5/2007 | Gannoe et al. |
| 7,234,624 B2 | 6/2007 | Gresham et al. |
| 7,235,089 B1 | 6/2007 | McGuckin, Jr. |
| RE39,841 E | 9/2007 | Bilotti et al. |
| 7,285,125 B2 | 10/2007 | Viola |
| 7,303,106 B2 | 12/2007 | Milliman et al. |
| 7,303,107 B2 | 12/2007 | Milliman et al. |
| 7,309,341 B2 | 12/2007 | Ortiz et al. |
| 7,322,994 B2 | 1/2008 | Nicholas et al. |
| 7,325,713 B2 | 2/2008 | Aranyi |
| 7,334,718 B2 | 2/2008 | McAlister et al. |
| 7,335,212 B2 | 2/2008 | Edoga et al. |
| 7,364,060 B2 | 4/2008 | Milliman |
| 7,398,908 B2 | 7/2008 | Holsten et al. |
| 7,399,305 B2 | 7/2008 | Csiky et al. |
| 7,401,721 B2 | 7/2008 | Holsten et al. |
| 7,401,722 B2 | 7/2008 | Hur |
| 7,407,075 B2 | 8/2008 | Holsten et al. |
| 7,410,086 B2 | 8/2008 | Ortiz et al. |
| 7,422,137 B2 | 9/2008 | Manzo |
| 7,422,138 B2 | 9/2008 | Bilotti et al. |
| 7,431,191 B2 | 10/2008 | Milliman |
| 7,438,718 B2 | 10/2008 | Milliman et al. |
| 7,455,676 B2 | 11/2008 | Holsten et al. |
| 7,455,682 B2 | 11/2008 | Viola |
| 7,481,347 B2 | 1/2009 | Roy |
| 7,494,038 B2 | 2/2009 | Milliman |
| 7,506,791 B2 | 3/2009 | Omaits et al. |
| 7,516,877 B2 | 4/2009 | Aranyi |
| 7,527,185 B2 | 5/2009 | Harari et al. |
| 7,537,602 B2 | 5/2009 | Whitman |
| 7,546,939 B2 | 6/2009 | Adams et al. |
| 7,546,940 B2 | 6/2009 | Milliman et al. |
| 7,547,312 B2 | 6/2009 | Bauman et al. |
| 7,556,186 B2 | 7/2009 | Milliman |
| 7,559,451 B2 | 7/2009 | Sharma et al. |
| 7,585,306 B2 | 9/2009 | Abbott et al. |
| 7,588,174 B2 | 9/2009 | Holsten et al. |
| 7,600,663 B2 | 10/2009 | Green |
| 7,611,038 B2 | 11/2009 | Racenet et al. |
| 7,635,385 B2 | 12/2009 | Milliman et al. |
| 7,669,747 B2 | 3/2010 | Weisenburgh, II et al. |
| 7,686,201 B2 | 3/2010 | Csiky |
| 7,694,864 B2 | 4/2010 | Okada et al. |
| 7,699,204 B2 | 4/2010 | Viola |
| 7,708,181 B2 | 5/2010 | Cole et al. |
| 7,717,313 B2 | 5/2010 | Criscuolo et al. |
| 7,721,932 B2 | 5/2010 | Cole et al. |
| 7,726,539 B2 | 6/2010 | Holsten et al. |
| 7,743,958 B2 | 6/2010 | Orban, III |
| 7,744,627 B2 | 6/2010 | Orban, III et al. |
| 7,770,776 B2 | 8/2010 | Chen et al. |
| 7,771,440 B2 | 8/2010 | Ortiz et al. |
| 7,774,889 B2 * | 8/2010 | Weaver ............... A47L 13/24 15/145 |
| 7,776,060 B2 | 8/2010 | Mooradian et al. |
| 7,793,813 B2 | 9/2010 | Bettuchi |
| 7,802,712 B2 | 9/2010 | Milliman et al. |
| 7,823,592 B2 | 11/2010 | Bettuchi et al. |
| 7,837,079 B2 | 11/2010 | Holsten et al. |
| 7,837,080 B2 | 11/2010 | Schwemberger |
| 7,837,081 B2 | 11/2010 | Holsten et al. |
| 7,845,536 B2 | 12/2010 | Viola et al. |
| 7,845,538 B2 | 12/2010 | Whitman |
| 7,857,187 B2 | 12/2010 | Milliman |
| 7,886,951 B2 | 2/2011 | Hessler |
| 7,896,215 B2 | 3/2011 | Adams et al. |
| 7,900,806 B2 | 3/2011 | Chen et al. |
| 7,909,039 B2 | 3/2011 | Hur |
| 7,909,219 B2 | 3/2011 | Cole et al. |
| 7,909,222 B2 | 3/2011 | Cole et al. |
| 7,909,223 B2 | 3/2011 | Cole et al. |
| 7,913,892 B2 | 3/2011 | Cole et al. |
| 7,918,377 B2 | 4/2011 | Measamer et al. |

(56) References Cited

U.S. PATENT DOCUMENTS

| | | |
|---|---|---|
| 7,922,062 B2 | 4/2011 | Cole et al. |
| 7,922,743 B2 | 4/2011 | Heinrich et al. |
| 7,931,183 B2 | 4/2011 | Orban, III |
| 7,938,307 B2 | 5/2011 | Bettuchi |
| 7,942,302 B2 | 5/2011 | Roby et al. |
| 7,951,166 B2 | 5/2011 | Orban, III et al. |
| 7,959,050 B2 | 6/2011 | Smith et al. |
| 7,967,181 B2 | 6/2011 | Viola et al. |
| 7,975,895 B2 | 7/2011 | Milliman |
| 8,002,795 B2 | 8/2011 | Beetel |
| 8,006,701 B2 | 8/2011 | Bilotti et al. |
| 8,006,889 B2 | 8/2011 | Adams et al. |
| 8,011,551 B2 | 9/2011 | Marczyk et al. |
| 8,011,554 B2 | 9/2011 | Milliman |
| 8,016,177 B2 | 9/2011 | Bettuchi et al. |
| 8,016,858 B2 | 9/2011 | Whitman |
| 8,020,741 B2 | 9/2011 | Cole et al. |
| 8,025,199 B2 | 9/2011 | Whitman et al. |
| 8,028,885 B2 | 10/2011 | Smith et al. |
| 8,038,046 B2 | 10/2011 | Smith et al. |
| 8,043,207 B2 | 10/2011 | Adams |
| 8,066,167 B2 | 11/2011 | Measamer et al. |
| 8,066,169 B2 | 11/2011 | Viola |
| 8,070,035 B2 | 12/2011 | Holsten et al. |
| 8,070,037 B2 | 12/2011 | Csiky |
| 8,096,458 B2 | 1/2012 | Hessler |
| 8,109,426 B2 | 2/2012 | Milliman et al. |
| 8,109,427 B2 | 2/2012 | Orban, III |
| 8,113,406 B2 | 2/2012 | Holsten et al. |
| 8,113,407 B2 | 2/2012 | Holsten et al. |
| 8,123,103 B2 | 2/2012 | Milliman |
| 8,128,645 B2 | 3/2012 | Sonnenschein et al. |
| 8,132,703 B2 | 3/2012 | Milliman et al. |
| 8,136,712 B2 | 3/2012 | Zingman |
| 8,146,790 B2 | 4/2012 | Milliman |
| 8,146,791 B2 | 4/2012 | Bettuchi et al. |
| 8,181,838 B2 | 5/2012 | Milliman et al. |
| 8,192,460 B2 | 6/2012 | Orban, III et al. |
| 8,201,720 B2 | 6/2012 | Hessler |
| 8,203,782 B2 | 6/2012 | Brueck et al. |
| 8,211,130 B2 | 7/2012 | Viola |
| 8,225,799 B2 | 7/2012 | Bettuchi |
| 8,225,981 B2 | 7/2012 | Criscuolo et al. |
| 8,231,041 B2 | 7/2012 | Marczyk et al. |
| 8,231,042 B2 | 7/2012 | Hessler et al. |
| 8,257,391 B2 | 9/2012 | Orban, III et al. |
| 8,267,301 B2 | 9/2012 | Milliman et al. |
| 8,272,552 B2 | 9/2012 | Holsten et al. |
| 8,276,802 B2 | 10/2012 | Kostrzewski |
| 8,281,975 B2 | 10/2012 | Criscuolo et al. |
| 8,286,845 B2 | 10/2012 | Perry et al. |
| 8,308,045 B2 | 11/2012 | Bettuchi et al. |
| 8,312,885 B2 | 11/2012 | Bettuchi et al. |
| 8,313,014 B2 | 11/2012 | Bettuchi |
| 8,317,073 B2 | 11/2012 | Milliman et al. |
| 8,317,074 B2 | 11/2012 | Ortiz et al. |
| 8,322,590 B2 | 12/2012 | Patel et al. |
| 8,328,060 B2 | 12/2012 | Jankowski et al. |
| 8,328,062 B2 | 12/2012 | Viola |
| 8,328,063 B2 | 12/2012 | Milliman et al. |
| 8,343,185 B2 | 1/2013 | Milliman et al. |
| 8,353,438 B2 | 1/2013 | Baxter, III et al. |
| 8,353,439 B2 | 1/2013 | Baxter, III et al. |
| 8,353,930 B2 | 1/2013 | Heinrich et al. |
| 8,360,295 B2 | 1/2013 | Milliman et al. |
| 8,365,974 B2 | 2/2013 | Milliman |
| 8,403,942 B2 | 3/2013 | Milliman et al. |
| 8,408,441 B2 | 4/2013 | Wenchell et al. |
| 8,413,870 B2 | 4/2013 | Pastorelli et al. |
| 8,413,872 B2 | 4/2013 | Patel |
| 8,418,905 B2 | 4/2013 | Milliman |
| 8,418,909 B2 | 4/2013 | Kostrzewski |
| 8,424,535 B2 | 4/2013 | Hessler et al. |
| 8,424,741 B2 | 4/2013 | McGuckin, Jr. et al. |
| 8,430,291 B2 | 4/2013 | Heinrich et al. |
| 8,430,292 B2 | 4/2013 | Patel et al. |
| 8,453,910 B2 | 6/2013 | Bettuchi et al. |
| 8,453,911 B2 | 6/2013 | Milliman et al. |
| 8,485,414 B2 | 7/2013 | Criscuolo et al. |
| 8,490,853 B2 | 7/2013 | Criscuolo et al. |
| 8,511,533 B2 | 8/2013 | Viola et al. |
| 8,551,138 B2 | 10/2013 | Orban, III et al. |
| 8,567,655 B2 | 10/2013 | Nalagatla et al. |
| 8,579,178 B2 | 11/2013 | Holsten et al. |
| 8,590,763 B2 | 11/2013 | Milliman |
| 8,590,764 B2 | 11/2013 | Hartwick et al. |
| 8,608,047 B2 | 12/2013 | Holsten et al. |
| 8,616,428 B2 | 12/2013 | Milliman et al. |
| 8,616,429 B2 | 12/2013 | Viola |
| 8,622,275 B2 | 1/2014 | Baxter, III et al. |
| 8,631,993 B2 | 1/2014 | Kostrzewski |
| 8,636,187 B2 | 1/2014 | Hueil et al. |
| 8,640,940 B2 | 2/2014 | Ohdaira |
| 8,662,370 B2 | 3/2014 | Takei |
| 8,663,258 B2 | 3/2014 | Bettuchi et al. |
| 8,672,931 B2 | 3/2014 | Goldboss et al. |
| 8,678,264 B2 | 3/2014 | Racenet et al. |
| 8,684,248 B2 | 4/2014 | Milliman |
| 8,684,250 B2 | 4/2014 | Bettuchi et al. |
| 8,684,251 B2 | 4/2014 | Rebuffat et al. |
| 8,684,252 B2 | 4/2014 | Patel et al. |
| 8,733,611 B2 | 5/2014 | Willman |
| 8,789,737 B2 | 7/2014 | Hodgkinson et al. |
| 9,883,860 B2 * | 2/2018 | Leimbach ............ A61B 17/068 |
| 2003/0111507 A1 | 6/2003 | Nunez |
| 2004/0059227 A1 | 3/2004 | Nita et al. |
| 2004/0105723 A1 * | 6/2004 | Takahashi ............... F16B 5/123 |
| | | 403/321 |
| 2004/0194324 A1 | 10/2004 | Youn-Chyuan |
| 2005/0051597 A1 | 3/2005 | Toledano |
| 2005/0107813 A1 | 5/2005 | Gilete Garcia |
| 2006/0000869 A1 | 1/2006 | Fontayne |
| 2006/0011698 A1 | 1/2006 | Okada et al. |
| 2006/0201989 A1 | 9/2006 | Ojeda |
| 2007/0027473 A1 | 2/2007 | Vresh et al. |
| 2007/0029363 A1 | 2/2007 | Popov |
| 2007/0060952 A1 | 3/2007 | Roby et al. |
| 2008/0179375 A1 * | 7/2008 | Scirica ............ A61B 17/07207 |
| | | 227/176.1 |
| 2008/0308605 A1 | 12/2008 | Scirica |
| 2009/0078336 A1 * | 3/2009 | Baudoux ................ B60K 15/04 |
| | | 141/311 R |
| 2009/0082777 A1 * | 3/2009 | Milliman ............. A61B 17/115 |
| | | 606/104 |
| 2009/0236392 A1 | 9/2009 | Cole et al. |
| 2009/0236398 A1 | 9/2009 | Cole et al. |
| 2009/0236401 A1 | 9/2009 | Cole et al. |
| 2009/0326540 A1 | 12/2009 | Estes |
| 2010/0019016 A1 | 1/2010 | Edoga et al. |
| 2010/0051668 A1 | 3/2010 | Milliman et al. |
| 2010/0084453 A1 | 4/2010 | Hu |
| 2010/0147923 A1 | 6/2010 | D'Agostino et al. |
| 2010/0163598 A1 | 7/2010 | Belzer |
| 2010/0224668 A1 | 9/2010 | Fontayne et al. |
| 2010/0230465 A1 | 9/2010 | Smith et al. |
| 2010/0258611 A1 | 10/2010 | Smith et al. |
| 2010/0264195 A1 | 10/2010 | Bettuchi |
| 2010/0308099 A1 * | 12/2010 | Marczyk .......... A61B 17/07207 |
| | | 227/175.1 |
| 2010/0327041 A1 | 12/2010 | Milliman et al. |
| 2011/0002734 A1 * | 1/2011 | Chen ..................... A47L 13/42 |
| | | 403/350 |
| 2011/0011916 A1 | 1/2011 | Levine |
| 2011/0114697 A1 | 5/2011 | Baxter, III et al. |
| 2011/0114700 A1 | 5/2011 | Baxter, III et al. |
| 2011/0144640 A1 | 6/2011 | Heinrich et al. |
| 2011/0147432 A1 | 6/2011 | Heinrich et al. |
| 2011/0186614 A1 | 8/2011 | Kasvikis |
| 2011/0192882 A1 | 8/2011 | Hess et al. |
| 2011/0276036 A1 | 11/2011 | Spranger et al. |
| 2012/0061448 A1 | 3/2012 | Zingman |
| 2012/0083778 A1 * | 4/2012 | McGaffigan ......... A61B 18/085 |
| | | 606/28 |
| 2012/0145755 A1 | 6/2012 | Kahn |

(56) References Cited

U.S. PATENT DOCUMENTS

| | | | |
|---|---|---|---|
| 2012/0193395 A1 | 8/2012 | Pastorelli et al. | |
| 2012/0193398 A1 | 8/2012 | Williams et al. | |
| 2012/0232339 A1 | 9/2012 | Csiky | |
| 2012/0273548 A1 | 11/2012 | Ma et al. | |
| 2012/0292371 A1* | 11/2012 | Nalagatla | A61B 17/1155 227/179.1 |
| 2012/0323226 A1* | 12/2012 | Chowaniec | A61B 17/072 606/1 |
| 2012/0325888 A1 | 12/2012 | Qiao et al. | |
| 2013/0015232 A1 | 1/2013 | Smith et al. | |
| 2013/0020372 A1 | 1/2013 | Jankowski et al. | |
| 2013/0020373 A1 | 1/2013 | Smith et al. | |
| 2013/0032628 A1 | 2/2013 | Li et al. | |
| 2013/0056516 A1 | 3/2013 | Viola | |
| 2013/0060258 A1 | 3/2013 | Giacomantonio | |
| 2013/0096591 A1 | 4/2013 | Hart et al. | |
| 2013/0105544 A1 | 5/2013 | Mozdzierz et al. | |
| 2013/0105546 A1 | 5/2013 | Milliman et al. | |
| 2013/0105551 A1 | 5/2013 | Zingman | |
| 2013/0123705 A1 | 5/2013 | Holm et al. | |
| 2013/0126580 A1 | 5/2013 | Smith et al. | |
| 2013/0138129 A1* | 5/2013 | Garrison | A61B 18/1445 606/170 |
| 2013/0153630 A1 | 6/2013 | Miller et al. | |
| 2013/0153631 A1 | 6/2013 | Vasudevan et al. | |
| 2013/0153633 A1 | 6/2013 | Casasanta, Jr. et al. | |
| 2013/0153634 A1 | 6/2013 | Carter et al. | |
| 2013/0153638 A1 | 6/2013 | Carter et al. | |
| 2013/0153639 A1 | 6/2013 | Hodgkinson et al. | |
| 2013/0175315 A1 | 7/2013 | Milliman | |
| 2013/0175318 A1 | 7/2013 | Felder et al. | |
| 2013/0175319 A1 | 7/2013 | Felder et al. | |
| 2013/0175320 A1 | 7/2013 | Mandakolathur Vasudevan et al. | |
| 2013/0181029 A1 | 7/2013 | Milliman | |
| 2013/0181035 A1 | 7/2013 | Milliman | |
| 2013/0181036 A1 | 7/2013 | Olson et al. | |
| 2013/0186930 A1 | 7/2013 | Wenchell et al. | |
| 2013/0193185 A1 | 8/2013 | Patel | |
| 2013/0193187 A1 | 8/2013 | Milliman | |
| 2013/0193190 A1 | 8/2013 | Carter et al. | |
| 2013/0193191 A1 | 8/2013 | Stevenson et al. | |
| 2013/0193192 A1 | 8/2013 | Casasanta, Jr. et al. | |
| 2013/0200131 A1 | 8/2013 | Racenet et al. | |
| 2013/0206816 A1 | 8/2013 | Penna | |
| 2013/0214027 A1 | 8/2013 | Hessler et al. | |
| 2013/0214028 A1 | 8/2013 | Patel et al. | |
| 2013/0228609 A1 | 9/2013 | Kostrzewski | |
| 2013/0240597 A1 | 9/2013 | Milliman et al. | |
| 2013/0240600 A1 | 9/2013 | Bettuchi | |
| 2013/0248581 A1 | 9/2013 | Smith et al. | |
| 2013/0277411 A1 | 10/2013 | Hodgkinson et al. | |
| 2013/0277412 A1 | 10/2013 | Gresham et al. | |
| 2013/0284792 A1 | 10/2013 | Ma | |
| 2013/0292449 A1 | 11/2013 | Bettuchi et al. | |
| 2013/0299553 A1 | 11/2013 | Mozdzierz | |
| 2013/0299554 A1 | 11/2013 | Mozdzierz | |
| 2013/0306701 A1 | 11/2013 | Olson | |
| 2013/0306707 A1 | 11/2013 | Viola et al. | |
| 2013/0319706 A1* | 12/2013 | Nicholas | B25F 3/00 173/29 |
| 2014/0001235 A1* | 1/2014 | Shelton, IV | A61B 17/07207 227/176.1 |
| 2014/0008413 A1 | 1/2014 | Williams | |
| 2014/0012317 A1 | 1/2014 | Orban et al. | |
| 2014/0088569 A1* | 3/2014 | Parihar | A61B 17/29 606/1 |
| 2014/0212833 A1* | 7/2014 | Mangelberger | A61C 1/0015 433/80 |
| 2014/0309677 A1 | 10/2014 | Baldwin | |
| 2015/0053746 A1* | 2/2015 | Shelton, IV | A61B 17/072 227/177.1 |
| 2015/0108201 A1 | 4/2015 | Williams | |
| 2015/0108728 A1* | 4/2015 | Nie | F16B 7/1418 280/47.371 |
| 2015/0148829 A1* | 5/2015 | Kimball | A61B 17/320068 606/169 |
| 2015/0173944 A1* | 6/2015 | Linsi | A61F 9/007 606/210 |
| 2015/0282807 A1* | 10/2015 | Chen | A61B 17/07207 227/180.1 |
| 2015/0320420 A1 | 11/2015 | Penna et al. | |
| 2016/0157856 A1* | 6/2016 | Williams | A61B 17/068 227/175.1 |
| 2016/0192934 A1* | 7/2016 | Williams | A61B 17/105 227/176.1 |
| 2016/0192939 A1* | 7/2016 | Sgroi, Jr. | A61B 17/1155 227/176.1 |
| 2017/0020526 A1* | 1/2017 | Scirica | A61B 17/105 |
| 2017/0079660 A1* | 3/2017 | Sgroi | A61B 17/068 |
| 2017/0224370 A1* | 8/2017 | Loreth | A61B 17/32002 |
| 2017/0363157 A1* | 12/2017 | Heine | A61B 17/162 |
| 2018/0008272 A1* | 1/2018 | Sgroi, Jr. | A61B 17/072 |

FOREIGN PATENT DOCUMENTS

| | | |
|---|---|---|
| CA | 908529 A | 8/1972 |
| CN | 201481477 U | 5/2010 |
| CN | 102783981 A | 11/2012 |
| DE | 1057729 B | 5/1959 |
| DE | 3301713 A1 | 7/1984 |
| EP | 0152382 A2 | 8/1985 |
| EP | 0173451 A1 | 3/1986 |
| EP | 0190022 A2 | 8/1986 |
| EP | 0282157 A1 | 9/1988 |
| EP | 0503689 A2 | 9/1992 |
| EP | 1190796 A1 | 3/2002 |
| EP | 1354560 A2 | 10/2003 |
| EP | 1631199 A1 | 3/2006 |
| EP | 2090245 A1 | 8/2009 |
| EP | 2524656 A2 | 11/2012 |
| EP | 2774549 A2 | 9/2014 |
| EP | 3031407 A1 | 6/2016 |
| EP | 3042619 A1 | 7/2016 |
| FR | 1136020 A | 5/1957 |
| FR | 1461464 A | 2/1966 |
| FR | 1588250 A | 4/1970 |
| FR | 2243758 A1 | 4/1975 |
| FR | 2443239 A1 | 7/1980 |
| GB | 1185292 A | 3/1970 |
| GB | 2016991 A | 9/1979 |
| GB | 2070499 A | 9/1981 |
| JP | S6025607 | 2/1985 |
| JP | 2011526804 A | 10/2011 |
| JP | 2013531509 A | 8/2013 |
| JP | 2013532559 A | 8/2013 |
| NL | 7711347 A | 4/1979 |
| SU | 1509052 A1 | 9/1989 |
| WO | 8706448 A1 | 11/1987 |
| WO | 8900406 A1 | 1/1989 |
| WO | 9006085 A1 | 6/1990 |
| WO | 9805261 A2 | 2/1998 |
| WO | 2001/054594 A1 | 8/2001 |
| WO | 2004107990 A1 | 12/2004 |
| WO | 2008/107918 A1 | 9/2008 |
| WO | 2012015917 A1 | 2/2012 |
| WO | 2014139327 A1 | 9/2014 |
| WO | 2014139440 A1 | 9/2014 |
| WO | 2014139442 A1 | 9/2014 |
| WO | 2014139467 A1 | 9/2014 |
| WO | 20140139442 A1 | 9/2014 |

OTHER PUBLICATIONS

European Search Report dated Sep. 1, 2016, issued in EP Application No. 16166326.

EP Examination Report dated Jun. 20, 2017, issued in EP Application No. 16150288.

Partial European Search Report dated Jan. 16, 2017, issued in EP Appln. No. 16180339.

European Search Report dated Nov. 30, 2016, issued in EP Application No. 16181395.

(56) References Cited

OTHER PUBLICATIONS

European Search Report dated May 23, 2017, issued in EP Application No. 16189648.
European Office Action dated Aug. 30, 2017, issued in EP Appln. No. 16 166 326.
U.S. Appl. No. 62/100,512, filed Jan. 7, 2015, inventor: Williams et al.
U.S. Appl. No. 62/150,913, filed Apr. 22, 2015, inventor: Penna et al.
U.S. Appl. No. 14/591,193, filed Jan. 7, 2015, inventor: Sgroi, Jr.
U.S. Appl. No. 14/810,811, filed Jul. 28, 2015, inventor: Sgroi, Jr., et al.
U.S. Appl. No. 14/805,547, filed Jul. 22, 2015, inventor: Scirica, et al.
U.S. Appl. No. 14/859,590, filed Sep. 21, 2015, inventor: Sgroi.
U.S. Appl. No. 14/804,814, filed Jul. 21, 2015, inventor: Williams et al.
European Search Report dated May 10, 2016, issued in EP Application No. 15198203.
European Search Report dated May 17, 2016, issued in EP Application No. 16150284.
European Office Action dated Jun. 25, 2018 in EP Appln. No. 16 166 326.
Chinese Office Action dated Feb. 2, 2019, issued in Japanese Appln. No. 201610252114.
Chinese Office Action dated Oct. 8, 2019 issued in CN Appln. No. 201610252114.
Australian Examination Report dated Oct. 31, 2019, issued in AU Appln. No. 2016201919.

* cited by examiner

FIG. 15

INTERLOCK ASSEMBLY FOR REPLACEABLE LOADING UNITS

CROSS-REFERENCE TO RELATED APPLICATIONS

This application claims the benefit of and priority to U.S. Provisional Patent Application Ser. No. 62/150,913 filed Apr. 22, 2015, the entire disclosure of which is incorporated by reference herein.

BACKGROUND

Technical Field

The present disclosure relates to surgical stapling devices including replaceable loading units. More particularly, the present disclosure relates to an interlock assembly for operably securing the replaceable loading units to an actuation assembly of the surgical stapling device and/or surgical adapter assembly.

Background of Related Art

Surgical devices for applying staples, clips, or other fasteners to tissue are well known. Endoscopic stapling devices include an actuation unit, i.e., a handle assembly for actuating the device and a shaft for endoscopic access, and a tool assembly disposed at a distal end of the shaft. Certain of these devices are designed for use with a replaceable loading unit which includes the tool assembly and houses the staples or fasteners. The replaceable loading unit may include staples of various sizes and the staples may be arranged in one or more configurations. After firing the stapling device with a replaceable loading unit, the user may detach the empty replaceable loading unit from the actuation unit, select and attach a second replaceable loading unit to the actuation unit, and fire the stapling device again. This process may be performed repeatedly during a surgical procedure.

Many of the stapling devices include an interlock assembly for selectively attaching the replaceable loading units to the actuation unit. The components of the interlock assemblies are typically located on the elongated bodies of the actuation unit or on an adapter assembly connected to the actuation unit. The sterilization and cleaning of the actuation units and adapter assemblies are complicated because of the location of the interlocking components on the elongated bodies or adapter assemblies.

Therefore, it would be beneficial to have a surgical device in which the components of the interlock assemblies are located on the loading units and, thus do not require sterilization.

SUMMARY

The present disclosure relates to an interlock assembly for operably securing replaceable loading units to an actuation assembly of a surgical stapling device and/or a surgical adapter assembly.

A loading unit including an interlock assembly for attaching the loading unit to a surgical stapling instrument is provided. The loading unit includes a shell member having a proximal end and a distal end. The shell member includes a cylindrical portion formed on the proximal end of the shell member and the distal end of the shell member supports a staple cartridge defining a plurality of staple retaining slots arranged in a pair of concentric rows. The cylindrical portion defines an opening formed therein. The loading unit also includes a collar member pivotally secured to the cylindrical portion. The collar member includes a locking shelf selectively receivable within the opening of the cylindrical portion of the shell member. The locking shelf is spaced from the opening of the cylindrical portion when the collar member is in an open position and the locking shelf is received through the opening in the cylindrical portion when the collar member is in a closed position.

In embodiments, the collar member may include a first end pivotally secured to the cylindrical portion of the shell member and a second end releasably securable to the cylindrical portion. The collar member may include a locking tab for releasably engaging the cylindrical portion of the shell member. The cylindrical portion of the shell member may include a notch for releasably receiving the locking tab. The collar member may include a resilient body configured for snap engagement about the cylindrical portion of the shell member. The collar member may include a C-shaped body.

In some embodiments, the locking shelf is configured to be received within an opening formed in a distal end of a surgical stapling instrument for securing the shell member to the distal end of the surgical stapling instrument. The locking shelf may include an inclined proximal portion for engaging a distal end of a surgical stapling instrument during receipt of the distal end of the surgical stapling instrument within the cylindrical portion of the shell assembly to move the collar member from the closed position to the open position.

The cylindrical portion of the shell member may include a recessed portion for releasably receiving the collar thereabout. The cylindrical portion of the shell member may define a depression adjacent the recessed portion thereof for facilitating engagement of an end of the collar member when the collar member is received about the recessed portion. The cylindrical portion of the shell member may be configured to receive a distal end of a surgical stapling instrument. The cylindrical portion of the shell member may include a raised feature for radially aligning and radially fixing the shell member relative to the distal end of the surgical stapling instrument and the raised feature may extend radially outward and longitudinally along an outer surface of the cylindrical portion. The raised feature may be configured for slidable receipt into a longitudinally extending keyway formed in the distal end of the surgical stapling instrument.

Also provided is a loading unit selectively connectable to a distal end of a surgical stapling instrument. The loading unit includes a shell member having a proximal end and a distal end. The shell member includes a cylindrical portion formed on the proximal end thereof the shell member. The cylindrical portion defines an opening formed therein. The loading unit also includes a staple cartridge defining a plurality of staple retaining slots arranged in a pair of concentric rows supported on the distal end of the shell member and a plurality of staples received within the staple retaining slots. The loading unit further includes a collar member pivotally secured to the cylindrical portion. The collar member includes a locking shelf selectively receivable within the opening of the cylindrical portion of the shell member.

In some embodiments, the locking shelf is spaced from the opening of the cylindrical portion when the collar member is in an open position and the locking shelf is received through the opening in the cylindrical portion when the collar member is in a closed position. The collar member may include a first end pivotally secured to the cylindrical portion of the shell member and a second end releasably securable to the cylindrical portion. The loading unit may include a locking tab formed on the second end of the collar member for releasably engaging the cylindrical portion of the shell member. The cylindrical portion of the shell member may include a notch for releasably receiving the locking tab. The collar member may include a resilient body configured for snap engagement about the cylindrical portion of the shell member.

BRIEF DESCRIPTION OF THE DRAWINGS

The accompanying drawings, which are incorporated in and constitute a part of this specification, illustrate embodiments of the disclosure and, together with a general description of the disclosure given above, and the detailed description of the embodiments given below, serve to explain the principles of the disclosure, wherein.

DETAILED DESCRIPTION

Embodiments of the presently disclosed interlock assembly will now be described in detail with reference to the drawings in which like reference numerals designate identical or corresponding elements in each of the several views. As is common in the art, the term "proximal" refers to that part or component closer to the user or operator, i.e. surgeon or clinician, while the term "distal" refers to that part or component further away from the user.

Figures 1, 2:
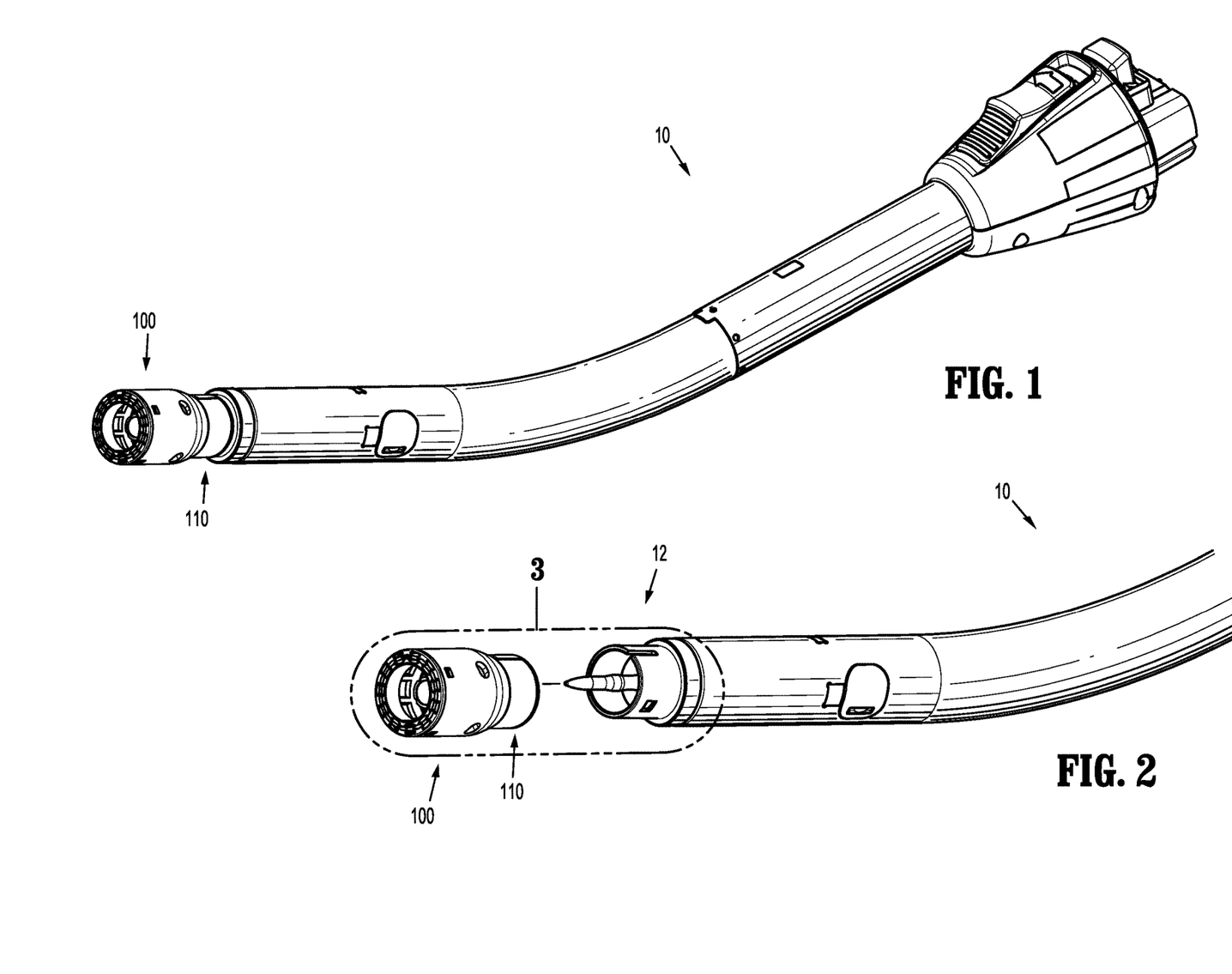
FIG. 1 is a perspective view of a replaceable loading unit, according to an embodiment of the present disclosure, secured to an adapter assembly.
FIG. 2 is a perspective view of the loading unit shown in FIG. 1 and a distal end of the adapter assembly shown in FIG. 1, prior to attachment of the loading unit to the adapter assembly.

With reference to FIGS. 1 and 2, an interlock assembly, according to an embodiment of the present disclosure, is shown generally as interlock assembly 110. The interlock assembly 110 is configured to operably secure a loading unit 100 to an adapter assembly 10. The adapter assembly 10 is configured to operably connect the loading unit 100 to a surgical stapling device (not shown). Although the interlock assembly 110 will be shown and described with reference to the loading unit 100 and the adapter assembly 10, it is envisioned that the interlock assembly 110 may be modified for use on different loading units and with different adapter assemblies. Alternatively, the interlock assembly 110 may be modified to be connected directly to an elongate body (not shown) of an actuation assembly (not shown).

The loading unit 100 and the adapter assembly 10 will only be described to the extent necessary to fully disclose the aspects of the present disclosure. For a detailed description of exemplary loading units and adapter assemblies, please refer to commonly owned U.S. Patent Application Publication No. 2013/0181035, the content of which is incorporated by reference herein in its entirety. Exemplary electromechanical surgical stapling devices for operating adapter assemblies and/or loading units are shown and described in U.S. Patent Application Publication No. 2012/0253329, the content of which is also incorporated by reference herein in its entirety.

Figure 3:
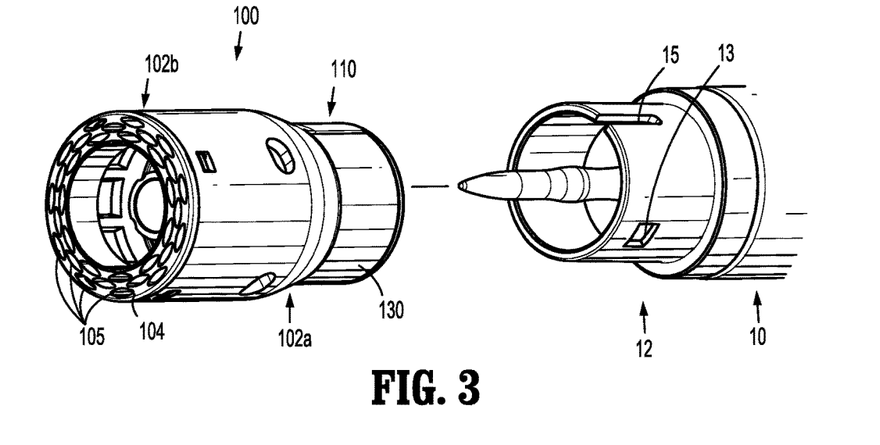
FIG. 3 is an enlarged view of the indicated area of detail shown in FIG. 2.

Turing briefly to FIG. 3, a distal end 12 of the adapter assembly 10 defines an attachment window 13 and a keyway or slot 15. The attachment window 13 extends through the annular wall of the distal end 12 of the adapter assembly 10 and is configured to receive a locking member of the interlock assembly 110 to longitudinally fix the loading unit 100 relative to the distal end 12 of the adapter assembly 10, as detailed below. The keyway 15 extends parallel to a longitudinal axis of the distal end 12 of the adapter assembly 10 and is configured to receive an alignment feature of the loading unit 100 to radially align and radially fix the loading unit 100 relative to the adapter assembly 10, as detailed below. As shown, the opening 13 and keyway 15 pass entirely through the annular wall of the distal end 12; however, it is contemplated that the opening 13 and/or the keyway 15 may instead define a notch (not shown) or a longitudinal groove (not shown) in the outer surface of the annular wall of the distal end 12 of the adapter assembly adapter 10.

With reference now to FIGS. 4-7, the loading unit 100 includes a shell member 102. The shell member 102 includes a proximal end 102a including an outer cylindrical portion 120 and a distal end 102b supporting a staple cartridge 104 defining a plurality of staple retaining slots 105 (FIG. 3). The staple retaining slots 105 may be arranged in a pair of concentric rows, as shown in FIG. 3. The interlock assembly 110 includes the outer cylindrical portion 120 of the shell member 102 and a collar member 130 pivotally secured to the outer cylindrical portion 120. The outer cylindrical portion 120 of the shell member 102 is configured to be received about the distal end 12 (FIG. 3) of the adapter assembly 10 (FIG. 3).

Figure 4:
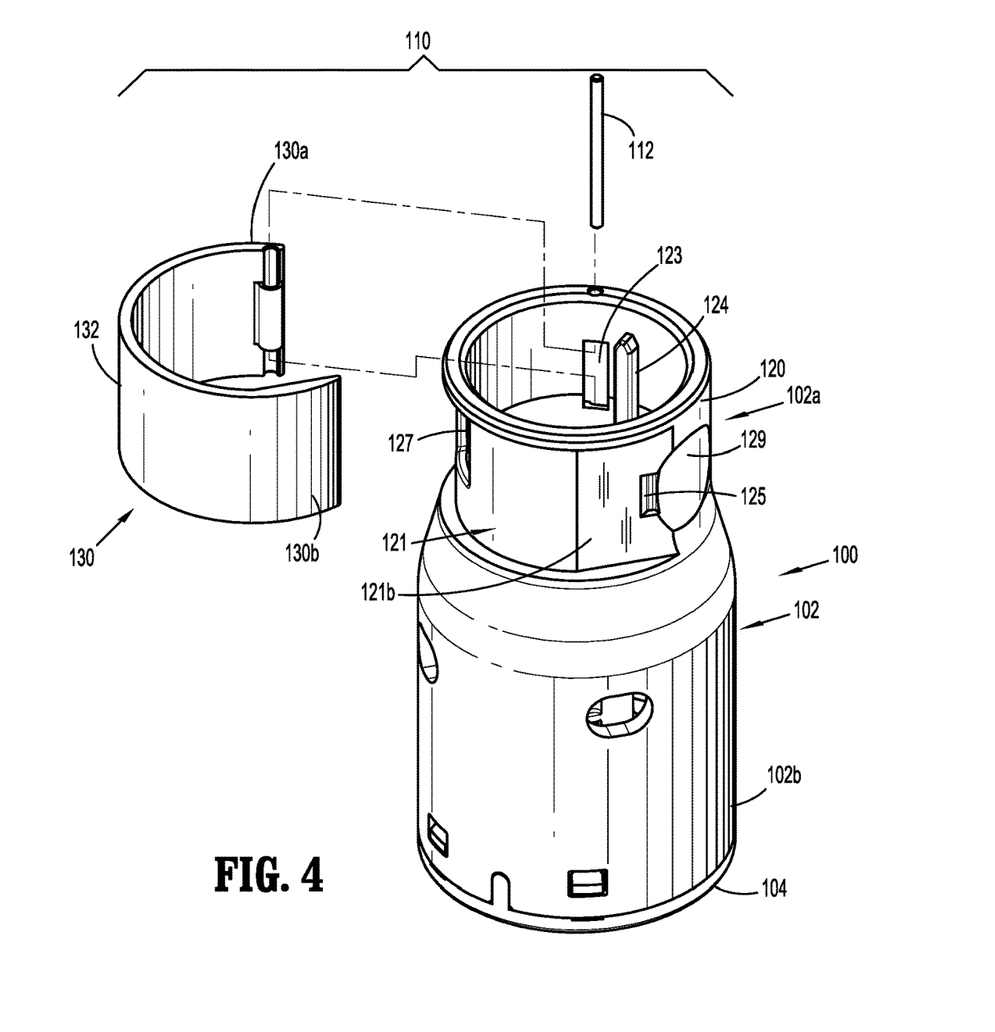
FIG. 4 is a side perspective view of the replaceable loading unit shown in FIG. 1 with a collar member separated.
Figure 5:
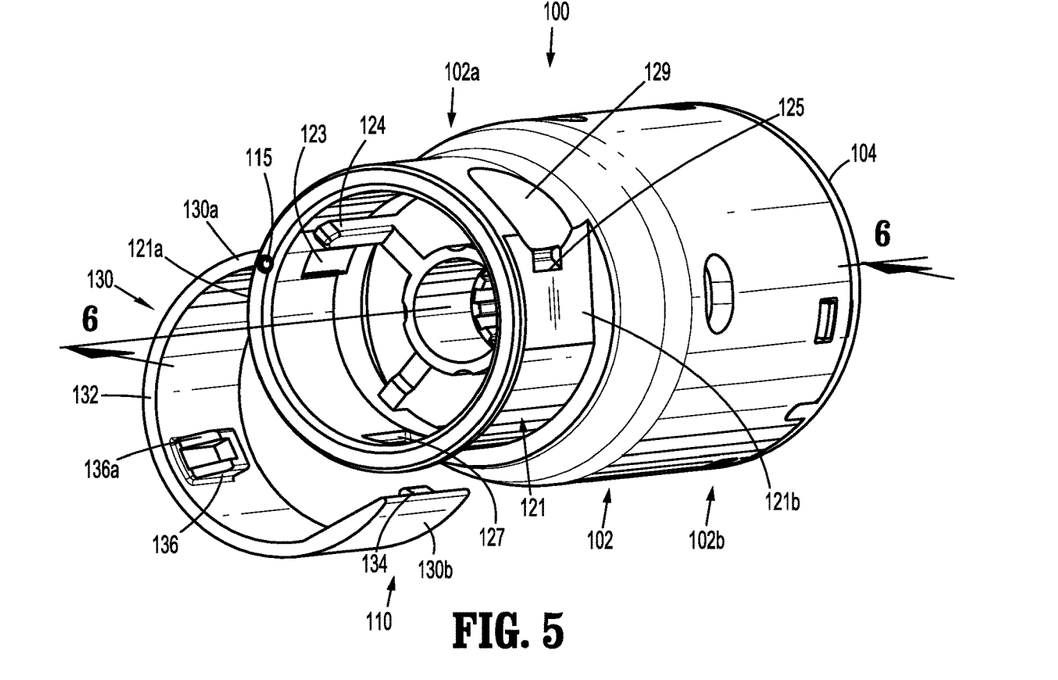
FIG. 5 is an end perspective view of the replaceable loading unit shown in FIG. 1, with an interlock assembly in a first or open position.
Figure 6:
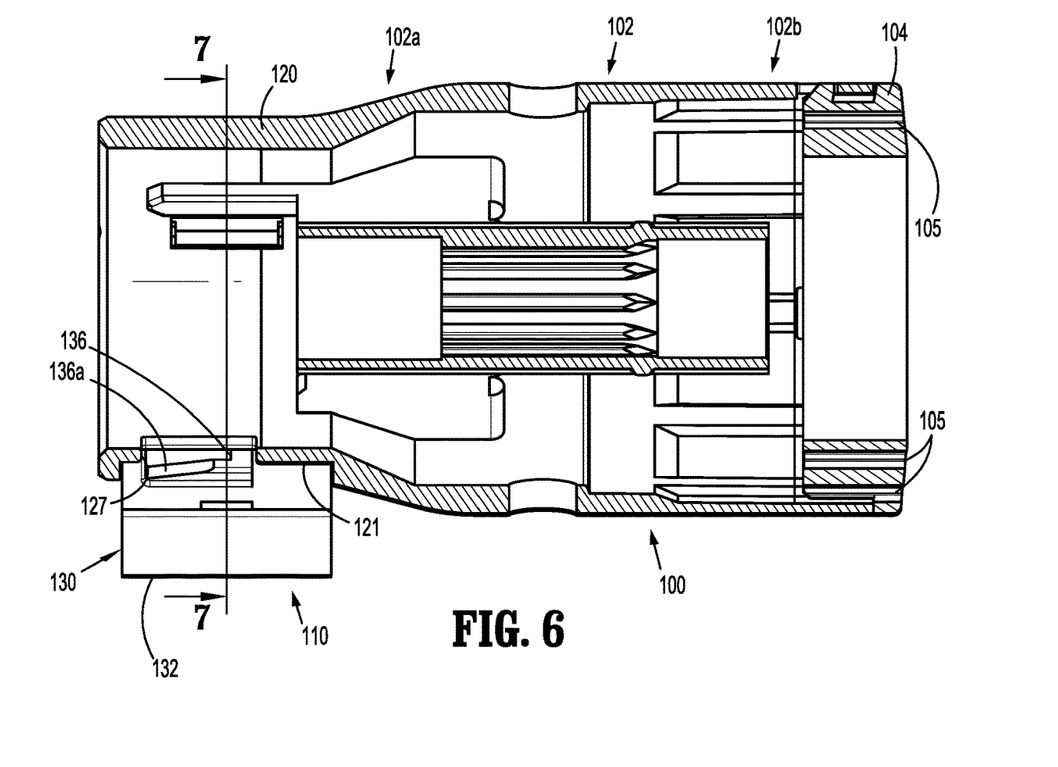
FIG. 6 is a cross-sectional view taken along line 6-6 shown in FIG. 5.
Figure 7:
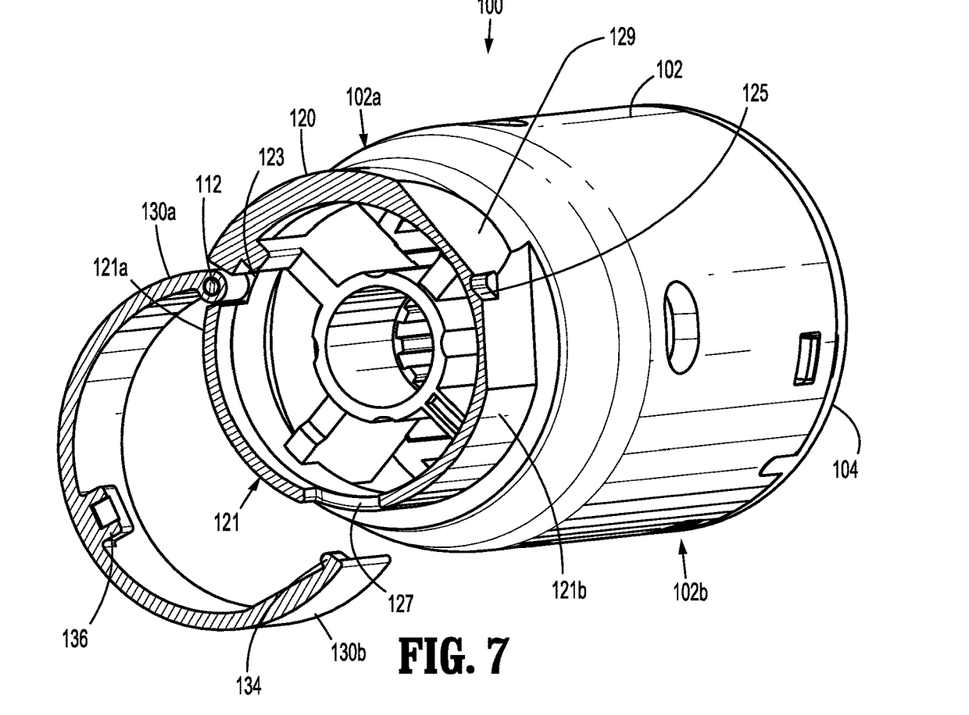
FIG. 7 is a cross-sectional view taken along line 7-7 shown in FIG. 6.
Figure 8:
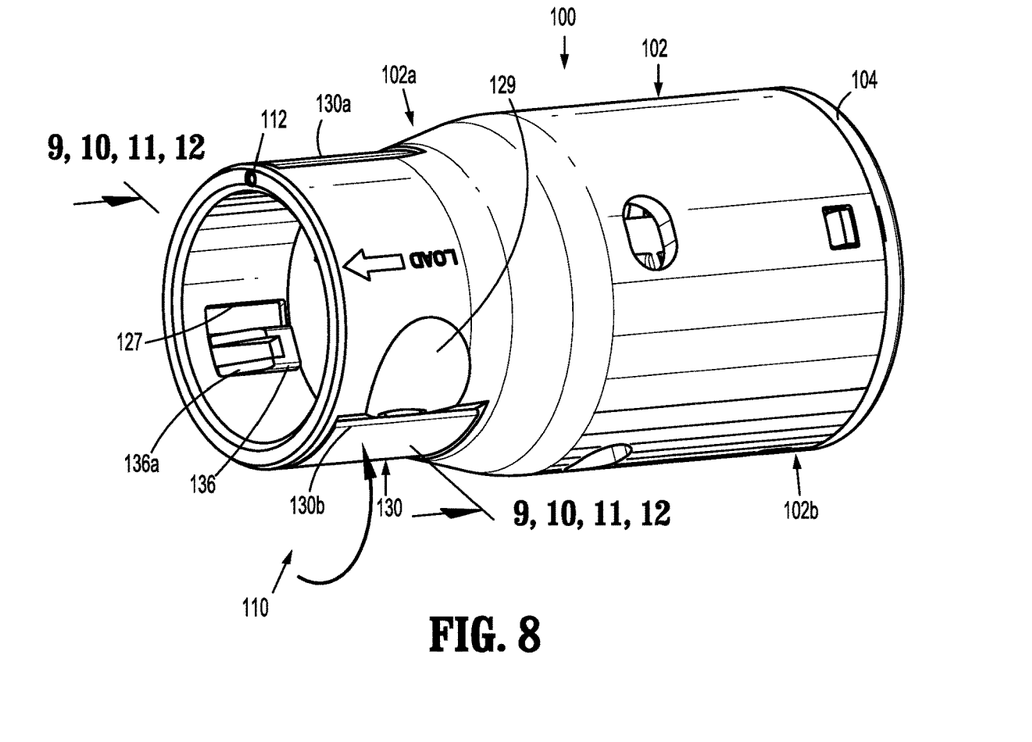
FIG. 8 is a side perspective view of the replaceable loading unit shown in FIG. 1, in a second or closed position.
Figure 9:
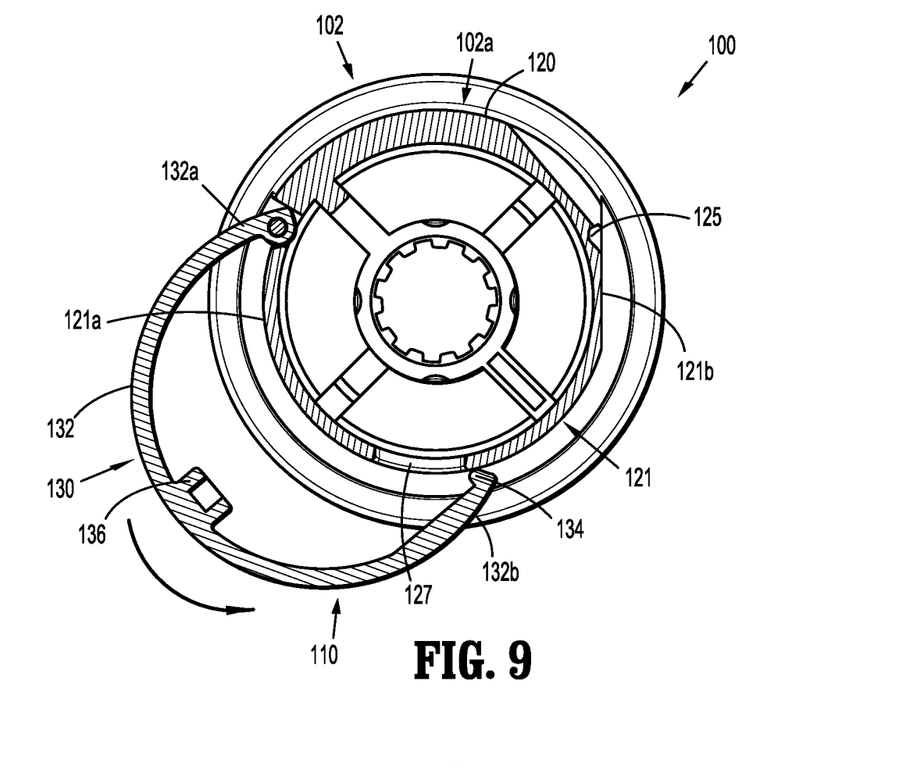
FIGS. 9-12 are cross-sectional views taken along respective lines 9-9, 10-10, 11-11, 12-12 shown in FIG. 8, with the interlock assembly at various stages between the open position and the closed position.
Figure 10:
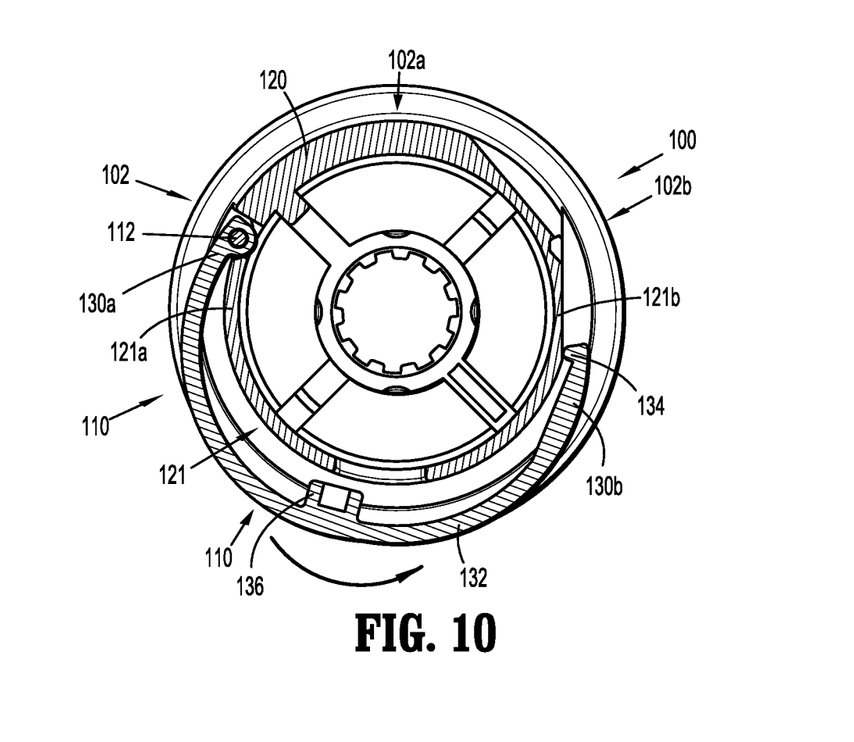

With particular reference to FIGS. 4 and 5, the outer cylindrical portion 120 of the shell member 102 includes a recessed portion or relief 121 that extends partially about an outer surface of the outer cylindrical portion 120 and is configured to receive the collar member 130 of the interlock assembly 110 thereabout. At a first end 121a of the recessed portion 121, the outer cylindrical portion 120 defines a cutout 123 for accommodating a first end 130a of the collar member 130. At a second end 121b of the recessed portion 121, the outer cylindrical portion 120 defines a notch 125 for accommodating a second end 130b of the collar member 130. Between the first and seconds ends 121a, 121b of the recessed portion 121, the outer cylindrical portion 120 defines an opening 127 for accommodating a locking feature of the collar member 130, e.g., locking shelf 136. Adjacent the second end 121b of the recessed portion 121, a depression 129 is defined in the outer surface of the outer cylindrical portion 120 to permit engagement of the second end 130b of the collar member 130 by a user. A raised feature 124 is formed on an inner surface of the outer cylindrical portion 120 of the shell member 102 and extends along a longitudinal axis of the outer cylindrical portion 120. As will be described in further detail below, the raised feature 124 is configured to be received within the keyway 15 (FIG. 3) of the distal end 12 (FIG. 3) of the adapter assembly 10 (FIG. 3) to radially align and radially fix the loading unit 100 relative to the adapter assembly 10.

With continued reference to FIGS. 4-7, the collar member 130 of the interlock assembly 110 includes a body 132 having a "C" shape profile and first and second ends 130a, 130b. The collar member 130 is formed of a resilient material and is configured to be releasably received about the recessed portion 121 of the outer cylindrical portion 120 of the shell member 102. The first end 130a of the collar member 130 is pivotally secured within the cutout 123 of the outer cylindrical portion 120 of the shell member 102 by a pivot pin 112. The second end 130b of the collar member 130 includes a locking tab 134 configured to be selectively received within the notch 125 in the outer cylindrical portion 120 of the shell member 102. The collar member 130 further includes a locking shelf 136 located between the first and second ends 130a, 130b thereof. The locking shelf 136 extends radially inward from the body 132 of the collar member 130 and is configured to be selectively received within the opening 127 in the outer cylindrical portion 120 of the shell member 102 when the collar member 130 is received about the recessed portion 121 of the outer cylindrical portion 120 of the shell member 102.

With reference to FIGS. 7-12, the collar member 130 is shown secured to the outer cylindrical portion 120 of the shell member 102. In a first or open position (FIG. 7), the second end 130b of the collar member 130 is pivoted away from the outer cylindrical portion 120 of the shell member 102. As the collar member 130 is moved to a second or locked position (FIG. 12), the second end 130b of the collar member 130 is pivoted towards the outer cylindrical portion 120 of shell member 102. As the locking tab 134 on the second end 130b of the collar member 130 engages the outer cylindrical portion 120 of the shell member 102, the body 132 of the collar member 130 flexes radially outward to permit the receipt of the collar member 130 about the outer cylindrical portion 120.

Figure 12:
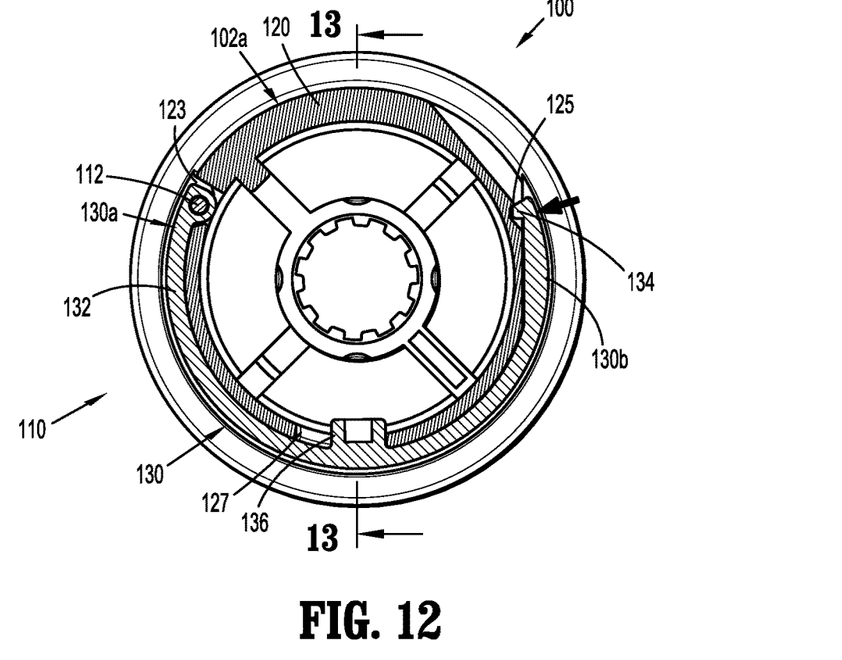

The collar member 120 is pivoted about the cylindrical body portion 120 of the shell member 102 until the locking tab 134 of the collar member 130 snaps into the notch 125 in the outer cylindrical portion 120 (FIG. 12). The locking tab 134 snaps into the notch 125 of the outer cylindrical portion 120 of the shell member 102 when the collar member 130 is received entirely about the recessed portion 121 of the outer cylindrical portion 120. The resiliency of the body 132 of the collar member 130 maintains the locking tab 134 of the collar member 130 within the notch 125 of the outer cylindrical portion 120.

Figure 11:
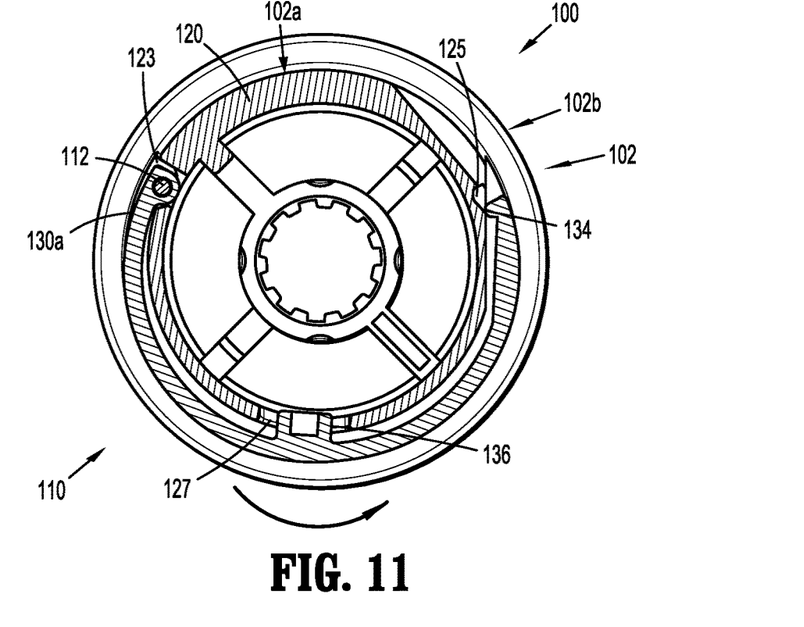

With particular reference to FIGS. 11 and 12, as the collar member 130 is pivotally received within the recessed portion 121 of the outer cylindrical portion 120 of the shell member 102, the locking shelf 136 of the collar member 130 is received within the opening 127 of the outer cylindrical portion 120.

To disengage the locking tab 134 of the collar member 130 from the outer cylindrical portion 120, the second end 130b of the collar member 130 is pulled away from the outer cylindrical portion 120 of the shell member 102. The depression 129 formed in the outer cylindrical portion 120 of the shell member 102 facilitates engagement or disengagement of the second end 130b of the collar member 130 with the outer cylindrical portion 120 of the shell member 102. Once the locking tab 134 is disengaged from the outer cylindrical portion 120 of the shell member 102, the collar member 130 may be pivoted about its first end 130a to retract the locking shelf 136 from within the opening 127 in the outer cylindrical portion 120.

Figure 13:
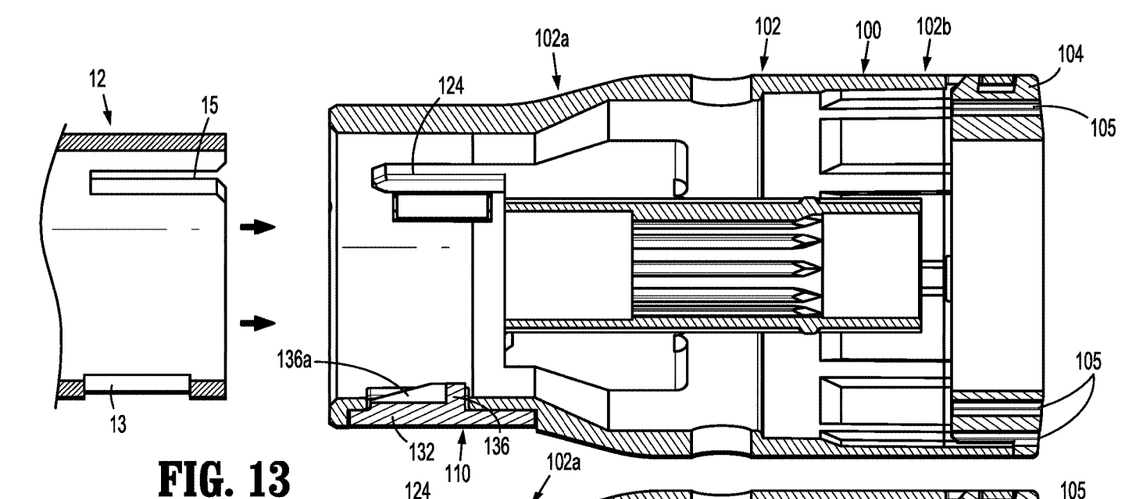
FIG. 13 is a cross-sectional view taken along line 13-13 shown in FIG. 12, prior to the replaceable loading unit shown in FIG. 1 being received on the distal end of the adapter assembly shown in FIG. 1.

The attachment of the loading unit 100 to the distal end 12 of the adapter assembly 10 will be described with reference to FIGS. 13-15. Referring initially to FIG. 13, the proximal end 102a of the shell member 102 of the loading unit 100 is positioned relative to the distal end 12 of the adapter assembly 10 such that the raised feature 124 on the inner surface of the outer cylindrical portion 120 of the shell assembly 102 is aligned with the keyway 15 of the distal end 12 of the adapter assembly 10. If the collar member 130 of the interlock assembly 110 is not already in the open position, the collar member 130 may be moved to the open position by engaging the second end 130b of the collar member 130 and disengaging the locking tab 134 of the collar member 130 from the outer cylindrical portion 120.

Figure 14:
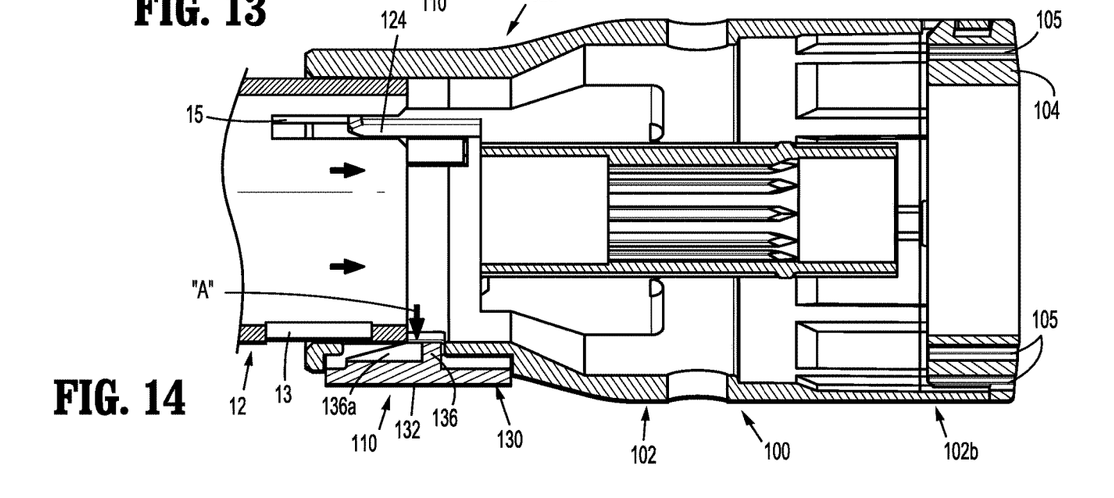
FIG. 14 is the cross-sectional view shown in FIG. 13 with the replaceable loading unit received on the distal end of the adapter assembly and the interlock assembly in the open position.

Alternatively, and as shown in FIG. 14, the locking shelf 136 includes a slanted or inclined proximal portion 136a which engages the distal end 12 of the adapter assembly 10 as the distal end 12 of the adapter assembly 10 is received within the outer cylindrical portion 120 of the shell member 102. As the inclined proximal portion 136a of the locking shelf 136 engages the distal end 12 of the adapter assembly 10, the force applied to the body 132 of the collar member 130, as indicated by arrow "A" in FIG. 14, causes the locking tab 134 of the collar member to unsnap or disengage from the outer cylindrical portion 120 of the shell member 102, thereby moving the interlocking assembly 110 to the open position and allowing the distal end 12 of the adapter assembly 10 to be completely received within the outer cylindrical portion 120 of the shell member 102.

Figure 15:
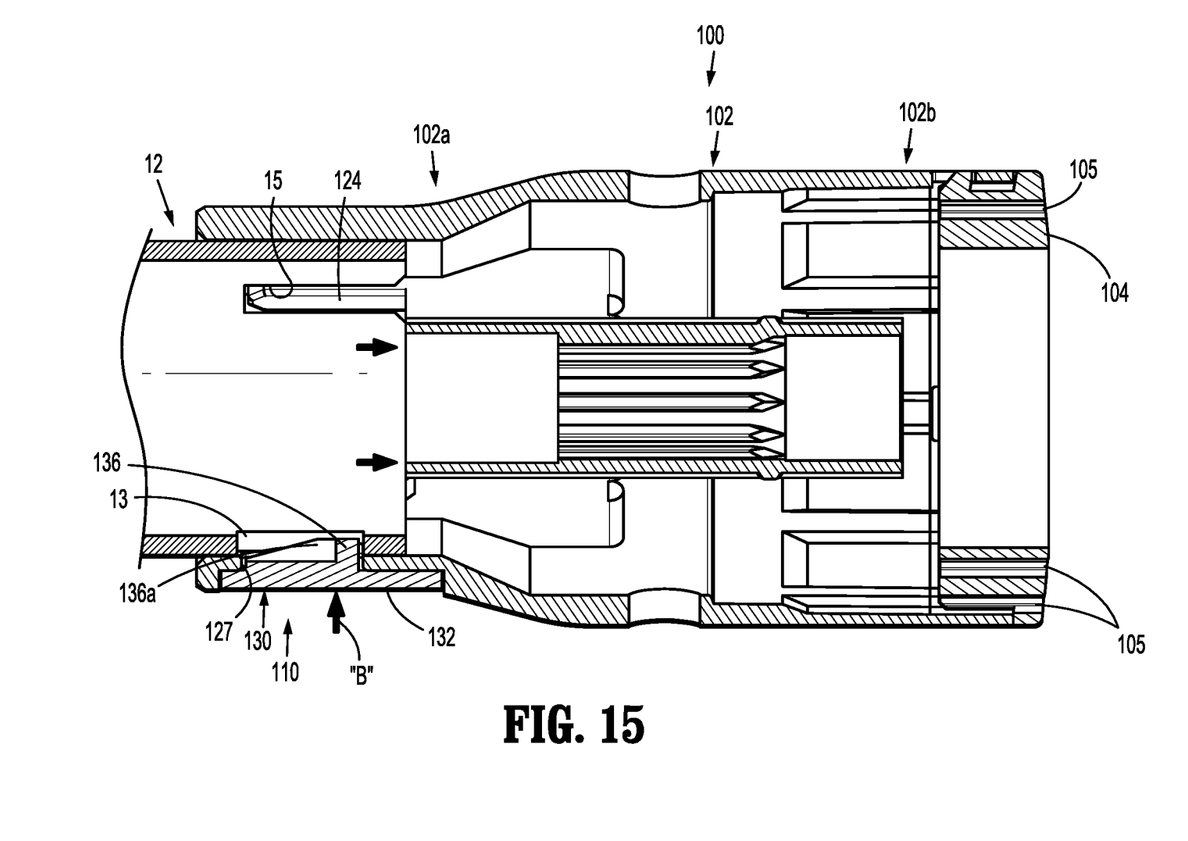
FIG. 15 is the cross-sectional view shown in FIG. 13 with the replaceable loading unit received on the distal end of the adapter assembly and the interlock assembly in the closed position.

With reference now to FIG. 15, after the distal end 12 of the adapter assembly 10 is completely received within the outer cylindrical portion 120 of the shell member 102, the collar member 130 of the interlock assembly 110 is moved to the locked position. In particular, the collar member 130 is pushed radially inwardly, as indicated by arrow "B" in FIG. 15, to receive the body 132 of the collar member 130 entirely about the recessed portion 121 of the outer cylindrical portion 120 of the shell member 102. As the body 132 of the collar member 130 is received about the recessed portion 121 of the outer cylindrical portion 120 of the shell member 102, the locking shelf 136 of the collar member 130 is received through the opening 127 in the outer cylindrical portion 120 of the shell member 102 and within the attachment window 13 in the distal end 12 of the adapter assembly 10. The receipt of the locking shelf 136 of the collar member 130 through the attachment window 13 of the adapter assembly 10 longitudinally fixes the loading unit 100 relative to the adapter assembly 10, thereby securing the loading unit 100 to the adapter assembly 10.

Once the loading unit 100 is secured to the distal end 12 of the adapter assembly 10, the surgical device (not shown) may be operated in a traditional manner. Following a stapling procedure, the loading unit 100 is separated from the adapter assembly 10 by first moving the interlock assembly 110 to the open position, as described above, then pulling the loading unit 100 longitudinally relative to the distal end 12 of the adapter assembly 10. The loading unit 100 may then be disposed of in a traditional manner.

Although the illustrative embodiments of the present disclosure have been described herein with reference to the accompanying drawings, it is to be understood that the disclosure is not limited to those precise embodiments, and that various other changes and modifications may be effected therein by one skilled in the art without departing from the scope or spirit of the disclosure.

What is claimed is:

1. A loading unit including an interlock assembly for attaching the loading unit to a surgical stapling instrument, the loading unit comprising:
a shell member including a proximal end and a distal end, the shell member including a cylindrical portion formed on the proximal end of the shell member, the cylindrical portion defining an outer circumference, the distal end of the shell member configured for supporting a staple cartridge defining a plurality of staple retaining slots arranged in a pair of concentric rows, the cylindrical portion defining an opening formed therein; and
a collar member pivotally secured to the cylindrical portion, the collar member including a locking shelf selectively receivable within the opening of the cylindrical portion of the shell member, wherein:
the locking shelf is spaced from the opening of the cylindrical portion when the collar member is in an open position; and
the locking shelf is received through the opening in the cylindrical portion and the collar member is disposed within the outer circumference of the cylindrical portion when the collar member is in a closed position.

2. The loading unit of claim 1, wherein the collar member includes a first end pivotally secured to the cylindrical portion of the shell member and a second end releasably securable to the cylindrical portion.

3. The loading unit of claim 1, wherein the collar member includes a locking tab for releasably engaging the cylindrical portion of the shell member.

4. The loading unit of claim 3, wherein the cylindrical portion of the shell member includes a notch for releasably receiving the locking tab.

5. The loading unit of claim 1, wherein the collar member includes a resilient body configured for snap engagement about the cylindrical portion of the shell member.

6. The loading unit of claim 1, wherein the collar member includes a C-shaped body.

7. The loading unit of claim 1, wherein the locking shelf is configured to be received within an opening formed in a distal end of a surgical stapling instrument for securing the shell member to the distal end of the surgical stapling instrument.

8. The loading unit of claim 1, wherein the locking shelf includes an inclined proximal portion for engaging a distal end of a surgical stapling instrument during receipt of the distal end of the surgical stapling instrument within the cylindrical portion of the shell assembly to move the collar member from the closed position to the open position.

9. The loading unit of claim 1, wherein the cylindrical portion of the shell member includes a recessed portion for releasably receiving the collar thereabout.

10. The loading unit of claim 9, wherein the cylindrical portion of the shell member defines a depression adjacent the recessed portion thereof for facilitating engagement of an end of the collar member when the collar member is received about the recessed portion.

11. The loading unit of claim 1, wherein the cylindrical portion of the shell member is configured to receive a distal end of a surgical stapling instrument.

12. The loading unit of claim 11, wherein the cylindrical portion of the shell member includes a raised feature for radially aligning and radially fixing the shell member relative to the distal end of the surgical stapling instrument.

13. The loading unit of claim 12, wherein the raised feature extends radially outward and longitudinally along an outer surface of the cylindrical portion, wherein the raised feature is configured for slidable receipt into a longitudinally extending keyway formed in the distal end of the surgical stapling instrument.

14. A loading unit selectively connectable to a distal end of a surgical stapling instrument, the loading unit comprising:
a shell member including a proximal end and a distal end, the shell member including a cylindrical portion formed on the proximal end thereof, the cylindrical portion defining a recessed portion and an opening in communication with the recessed portion;
a staple cartridge defining a plurality of staple retaining slots arranged in a pair of concentric rows supported on the distal end of the shell member;
a plurality of staples received within the staple retaining slots; and
a collar member pivotally secured to the cylindrical portion, the collar member being selectively receivable in the recessed portion of the cylindrical portion and including a locking shelf selectively receivable within the opening of the cylindrical portion of the shell member when the collar member is received within the recessed portion.

15. The loading unit of claim 14, wherein the locking shelf is spaced from the opening of the cylindrical portion when the collar member is in an open position and the locking shelf is received through the opening in the cylindrical portion when the collar member is in a closed position.

16. The loading unit of claim 14, wherein the collar member includes a first end pivotally secured to the cylindrical portion of the shell member and a second end releasably securable to the cylindrical portion.

17. The loading unit of claim 16, further comprising a locking tab formed on the second end of the collar member for releasably engaging the cylindrical portion of the shell member.

18. The loading unit of claim 17, wherein the cylindrical portion of the shell member includes a notch for releasably receiving the locking tab.

19. The loading unit of claim 14, wherein the collar member includes a resilient body configured for snap engagement about the cylindrical portion of the shell member.

20. The loading unit of claim 14, wherein the cylindrical portion defines an outer circumference, the collar member being disposed within the outer circumference of the cylindrical portion when the collar member is received within the recessed portion.

* * * * *

UNITED STATES PATENT AND TRADEMARK OFFICE
CERTIFICATE OF CORRECTION

PATENT NO. : 10,881,408 B2
APPLICATION NO. : 15/074045
DATED : January 5, 2021
INVENTOR(S) : Penna et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1091 days.

Signed and Sealed this
Seventh Day of February, 2023

Katherine Kelly Vidal
*Director of the United States Patent and Trademark Office*